(12) United States Patent
McAndrew et al.

(10) Patent No.: US 6,421,127 B1
(45) Date of Patent: Jul. 16, 2002

(54) METHOD AND SYSTEM FOR PREVENTING DEPOSITION ON AN OPTICAL COMPONENT IN A SPECTROSCOPIC SENSOR

(75) Inventors: James J. F. McAndrew, Lockport, IL (US); Benjamin Jurcik, St. Remy les Chevreuse (FR); Carol Schnepper, Tulsa, OK (US); Ronald Inman, Lyons, IL (US); Dmitry Znamensky, Darien, IL (US); Tracey Jacksier, Lisle, IL (US)

(73) Assignee: American Air Liquide, Inc., Fremont, CA (US)

( * ) Notice: Subject to any disclaimer, the term of this patent is extended or adjusted under 35 U.S.C. 154(b) by 0 days.

(21) Appl. No.: 09/613,806

(22) Filed: Jul. 11, 2000

Related U.S. Application Data
(60) Provisional application No. 60/144,181, filed on Jul. 19, 1999.

(51) Int. Cl.[7] .......................... G01N 21/03; G01N 21/31
(52) U.S. Cl. ...................... 356/437; 356/440; 356/246; 359/509; 359/512
(58) Field of Search ................................ 356/246, 437, 356/440; 359/507, 509, 512

(56) References Cited

U.S. PATENT DOCUMENTS

| | | | |
|---|---|---|---|
| 4,443,072 A | 4/1984 | Ballard | ........................ 356/246 |
| 5,360,980 A | 11/1994 | Borden et al. | |
| 5,565,985 A | 10/1996 | Fishkin et al. | |
| 5,949,537 A | * 9/1999 | Inman et al. | ................ 356/246 |

FOREIGN PATENT DOCUMENTS

| | | |
|---|---|---|
| EP | 0 596 605 | 5/1994 |
| EP | 0 768 521 | 4/1997 |
| EP | 0 768 525 | 4/1997 |
| FR | 2 751 089 | 7/1996 |
| JP | 59120825 | 7/1984 |
| WO | WO99/02969 | 1/1999 |

OTHER PUBLICATIONS

Austrian Search Report and Written Opinion issued in Singapore Application No. SG 200004043-6.
European Search Report issued in Application No. EP 00 40 2043.

\* cited by examiner

*Primary Examiner*—F. L. Evans
(74) *Attorney, Agent, or Firm*—Linda K. Russell (57) ABSTRACT

Provided are novel methods of preventing deposition on an optical component in an absorption spectroscopy measurement cell. The methods involve performing an absorption spectroscopy measurement of a sample gas introduced into the cell, and introducing a flow of purge gas from a purge gas inlet pipe across a critical surface of the optical element at a velocity effective to prevent deposition on the critical surface. The gas inlet is disposed adjacent said critical surface. Also provided are devices for practicing the inventive method, measurement cells useful in absorption spectroscopy measurements, apparatuses for performing an absorption spectroscopy measurement and semiconductor processing apparatuses. The invention allows for the performance of accurate spectroscopic measurements. Because deposits are prevented from forming on the surface of an optical element, interference therefrom can effectively be avoided.

31 Claims, 9 Drawing Sheets

FIG. 2B
VIEW A-A'

METHOD AND SYSTEM FOR PREVENTING DEPOSITION ON AN OPTICAL COMPONENT IN A SPECTROSCOPIC SENSOR

CROSS REFERENCE TO RELATED APPLICATION

This application claims the benefit under 35 U.S.C. §119 (e) to provisional application No. 60/144,181, filed Jul. 19, 1999, the entire contents of which are incorporated herein by reference.

BACKGROUND OF THE INVENTION

1. Field of the Invention

The present invention relates to novel methods and devices for preventing deposition on an optical component in an absorption spectroscopy measurement cell. The present invention also relates to measurement cells useful in absorption spectroscopy measurement. The invention further relates to apparatuses for performing an absorption spectroscopy measurement, and to semiconductor processing apparatuses.

2. Description of the Related Art

Semiconductor integrated circuits (ICs) are manufactured by a series of processes, many of which involve the use of gases. Included among such processes are etching, diffusion, chemical vapor deposition (CVD), ion implantation, sputtering and rapid thermal processing. The use of an in-line absorption spectroscopy cell to monitor impurities in such processes is described, for example, in U.S. Pat. No. 5,963,336, to McAndrew et al, the contents of which are incorporated herein by reference.

The sensitivity of detection of gas phase molecular species by absorption spectroscopy increases as the length of the light path through the sample increases, for constant pressure and concentration. The intensity of light reaching the detector is given by Beer's Law as follows:

$$I = I_o \cdot e^{-\alpha cPl}$$

where $I_o$ is the intensity of the incident radiation, $\alpha$ is the absorptivity, l is the pathlength through the sample, c is the concentration of the impurity in the sample (by volume) and P is the total pressure of the sample. For small absorptions, the amount of light absorbed is given by $$I - I_o = \alpha cPl$$

In order to make l large, it is frequently impractical to place the light source and detector very far apart. Thus, "folded" light paths are often used, in which mirrors reflect the light back and forth through the sample gas many times.

Figure 1:
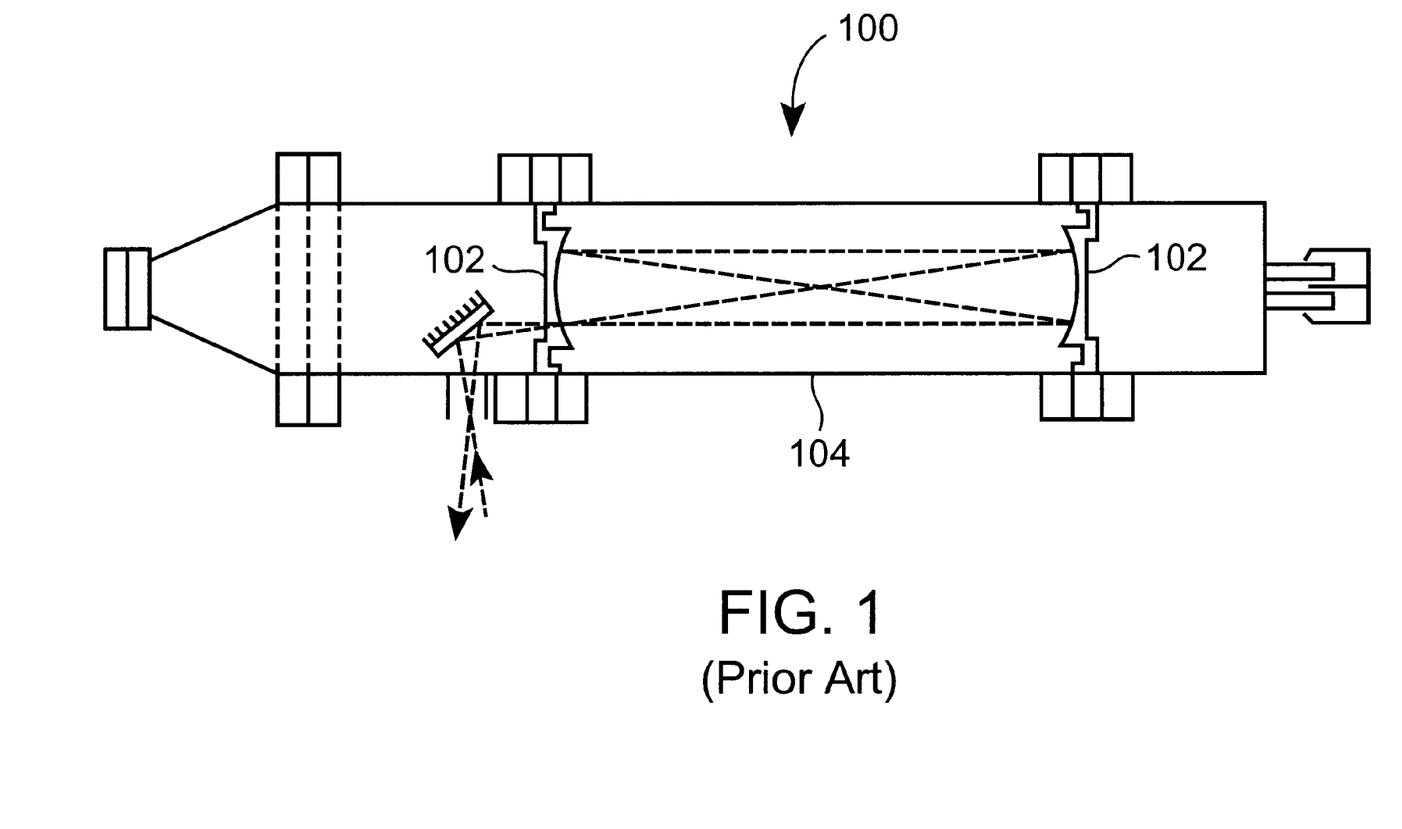
FIG. 1 is a conventional absorption spectroscopy cell according to the Herriott design.

The Herriott design is often preferred for tunable diode laser absorption spectroscopy (TDLAS). As shown in FIG. 1, the exemplary Herriott cell 100 uses two curved mirrors 102 mounted at opposite ends of a usually cylindrical gas sample cell 104. Other types of multi-pass cells are also known. Simple multi-pass arrangements are often used, such as described in U.S. Pat. No. 3,524,066, to Blakkan, and U.S. Pat. No. 5,173,749, to Tell et al, the contents of which patents are herein incorporated by reference. A planar polygonal multipass cell is described in U.S. Pat. No. 5,818,578, to Inman et al, the contents of which are herein incorporated by reference.

Intracavity laser absorption spectroscopy (see W. Brunner and H. Paul "On the theory of selective intracavity absorption" Optics Communications 12(3) 252 (1974)), also known as intracavity laser spectroscopy (see U.S. Pat. No. 5,723,864, to Atkinson et al) is based upon the principle of absorption of laser light within a laser cavity. Cavity ring-down spectroscopy (see A. O'Keefe et al, "Cavity ring-down spectrometer for absorption measurements using pulsed laser sources" Rev. Sci. Instrum. 59(12) 2544 (1988) and U.S. Pat. No. 5,973,864, to Lehmann et al) is based upon laser light absorption within an external cavity. Both of these methods are considered sophisticated types of absorption spectroscopy. They provide very high sensitivity and rely upon the probe light beam making many passes through the cavity and therefore upon very highly reflective optics.

Various gases used in the semiconductor manufacturing processes referenced above are highly reactive and tend to form deposits on surfaces with which they come into contact, especially under conditions used in IC fabrication, such as high temperature or plasma conditions. When an in-line spectroscopic sensor is used to monitor a process in such aggressive atmospheres, deposits from the process gases tend to form on surfaces of the sensor, including, for example, on optical components such as light reflective mirrors and light transmissive windows.

Deposits formed on the optical components of a spectroscopic cell can adversely impact the sensitivity and operation of the sensor. For example, deposits formed on the reflective surfaces of the mirrors can reduce their reflectivity and hence the light intensity which reaches the detector after multiple reflections of the light beam. Likewise, the formation of deposits on the light transmissive window(s), through which the light beam enters and exits the measurement cell, reduces the light intensity reaching the detector. Such reduction in light intensity decreases the measurement sensitivity and may eventually lead to a condition in which the sensor does not function at all.

Deposits on the mirrors and light transmissive windows are conventionally removed by disassembling the sensor and mechanically/chemically cleaning the contaminated components. Such maintenance, however, is inconvenient and expensive. Avoidance or minimization of the deposits is therefore desirable.

U.S. Pat. No. 5,360,980, to Borden et al, discloses a particle sensor for monitoring the particle level of a process chamber by light scattering. To prevent contamination by corrosive or coating species in the effluent from the process, a gas purge line allows a flow of gas to purge the optical components at a flux not less than the flux of gas being removed from the process chamber in the exhaust line. Use of a purge gas with such a high flowrate is undesirable because of the increased load on the vacuum pump. Consequently, replacement of the exhaust line with one of larger diameter, and possibly replacement of a vacuum pump with one of higher capacity may be required. Additionally, the possibility of back-contamination of the process chamber is increased.

To meet the requirements of the semiconductor processing industry and to overcome at least some of the disadvantages of the related art, it is an object of the present invention to provide a novel method of and device for preventing deposition on an optical component useful in absorption spectroscopy. The problems associated with the formation of deposits on optical components, such as mirrors and light transmissive windows in absorption spectroscopy measurement cells can thereby be avoided or conspicuously ameliorated. In particular, the invention can minimize the flow of purge gas, employing a flux less than that of gas being exhausted from the process chamber. A minimum flow of purge gas can thereby be employed.

It is a further object of the present invention to provide an in-line cell useful in absorption spectroscopy and to provide an apparatus for performing an absorption spectroscopy measurement which comprise the novel device for preventing deposition.

It is further an object of the present invention to provide a semiconductor processing apparatus which comprises the inventive in-line cell.

Other objects and aspects of the present invention will become apparent to one of ordinary skill in the art on a review of the specification, drawings and claims appended hereto.

SUMMARY OF THE INVENTION

According to a first aspect of the present invention, novel methods of preventing deposition on an optical component in an absorption spectroscopy measurement cell, such as a tunable diode laser, an intra-cavity or a cavity ring-down spectroscopy cell, are provided. The inventive methods comprise performing an absorption spectroscopy measurement of a sample gas introduced into the cell, and introducing a flow of purge gas from a purge gas inlet pipe across a critical surface of the optical element at a velocity effective to prevent deposition on the critical surface. The gas inlet is disposed adjacent said critical surface.

According to a further aspect of the invention, devices for preventing deposition on an optical component useful in an absorption spectroscopy measurement cell are provided. The inventive devices comprise a purge gas inlet pipe for introducing a flow of purge gas across a critical surface of the optical element at a velocity effective to prevent deposition on the critical surface. The gas inlet is disposed adjacent said critical surface.

According to a further aspect of the invention, measurement cells useful in absorption spectroscopy measurement are provided. The measurement cells comprise, in addition to a device for preventing deposition as described above, a sample gas inlet, a sample gas outlet, a sample region, a light entry port and a light exit port being the same or separate ports. Each port is in optical communication with the sample region and contains a light transmissive window.

In accordance with a further aspect of the invention, apparatuses for performing an absorption spectroscopy measurement are provided. The apparatuses comprise the a measurement cell as described above, a light source for generating a light beam which passes through the light entry port into the cell, and a detector for measuring the light beam exiting the cell through the light exit port.

In accordance with a further aspect of the invention, semiconductor processing apparatuses are provided. The apparatuses comprise a semiconductor processing apparatus comprising a substrate processing chamber and an exhaust line connected thereto, and an apparatus for performing an absorption spectroscopy measurement as described above.

The invention is particularly applicable to in-situ absorption spectroscopy measurements which are useful, for example, to accurately and sensitively measure the concentration of gas phase molecular impurities, such as, e.g., methane, moisture (water vapor) and carbon dioxide, in a sample. Through the invention, the surfaces of optical elements, such as mirrors and light transmissive windows, can be maintained in a deposit-free state.

In the case of mirrors employed in absorption spectroscopy measurements, the invention ensures that reflectivity of the surface of the mirror is not reduced due to deposits formed thereon. Similarly, in the case the surface of the optical component belongs to a light transmissive window, the invention ensures that the light transmissive characteristics of the window are not degraded.

The invention has particular applicability to the prevention of deposition on optics used for in-situ measurements of gas composition, such that the clean gas flow is directed over critical surfaces of the optics and the flow of clean gas is minimized by appropriate design of the gas inlet and control of the gas velocity.

BRIEF DESCRIPTION OF THE DRAWINGS

The objects and advantages of the invention will become apparent from the following detailed description of the preferred embodiments thereof in connection with the accompanying drawings, in which.

DETAILED DESCRIPTION OF THE PREFERRED EMBODIMENTS OF THE INVENTION

Figure 2A:
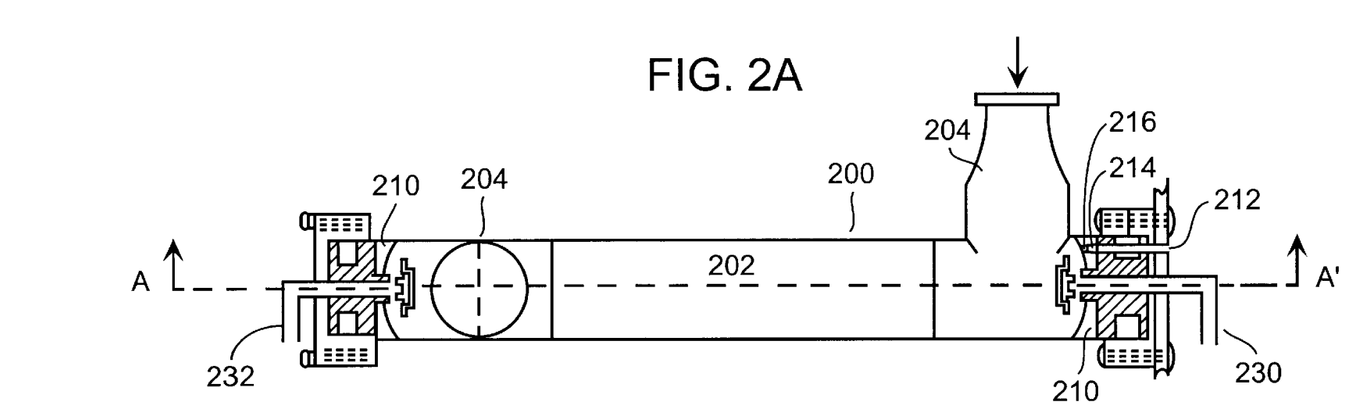
FIGS. 2A and 2B are top plan and side-sectional views, respectively, of an exemplary in-line cell in accordance with a further aspect of the invention.
Figure 2B:
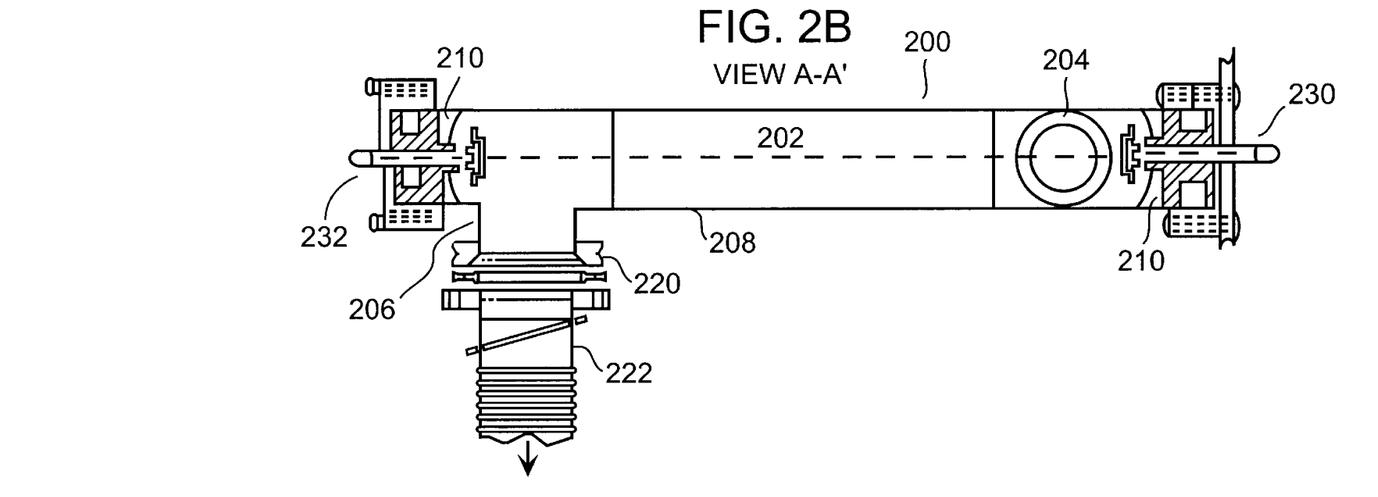

FIGS. 2A and 2B illustrate cross-sectional views of an exemplary in-line cell 200 useful in absorption spectroscopy according to one aspect of the invention. While this exemplary cell is of the Herriott type of multipass cell, it should be clear that the inventive concepts described hereinbelow are in no way limited thereto, and can readily be applied to other forms of cells which employ optical elements, for example, intra-cavity and cavity ring-down cells.

The in-line cell 200 includes a sample region 202. The walls of the cell preferably define a substantially cylindrical space through which the sample gas flows. The sample gas flows through the cell from a sample inlet port 204 into sample region 202, and out of the cell through exhaust port 206.

The inlet port 204 is to be connected to a source of the sample to be measured. As described below, inlet port 204 can advantageously be connected to an exhaust line of a semiconductor processing tool which allows the performance of in-situ measurements. In this way, concentrations of molecular gas species in the processing tool exhaust can be measured. The exhaust port 206 is typically connected to the foreline of a vacuum pump or other exhausting means, for example a fan or blower. Connection of the inlet and exhaust ports with the sample source and the exhausting means, respectively, can be made using known means, such as with flanges and flexible hoses.

The cell can include one or more mirrors 210 for reflecting a light beam through the sample region. In this exemplified embodiment, a plurality of preferably curved mirrors 210 are disposed along the interior of the cell. It is noted that the mirror structure will vary depending on whether it functions as part of a light beam entry/exit structure. Each of the mirrors has a light reflective surface facing the sample region, and is disposed such that a light beam entering the cell is reflected from one mirror to another through the sample region until each mirror has reflected the light beam at least one time prior to exiting the cell.

The light reflective surfaces are preferably a polished metal. As a high reflectivity of these surfaces is desirable, the surfaces can be coated with one or more layers of a reflective material such as gold, other metallic layers or a highly reflective dielectric coating, in order to enhance the reflectivity thereof.

The cell further includes a light entry and exit port 212 for allowing a light beam to pass into and out of the cell. As illustrated, mirror 210 includes an aperture 214 extending therethrough, which forms part of the light entry/exit port, through which the light beam can pass. While the exemplary embodiment shows a single port through which the light beam enters and exits the cell, a plural port structure is also envisioned. Thus, the light beam can enter and exit the cell through the same or different ports in the cell, and can enter and/or exit the cell through plural light entry or light exit ports. Further, the ports can be disposed on the same side or different sides of the cell.

The light entry/exit port 212 contains a light transmissive window 216 which allows the light beam to pass into and out of the cell and through the sample region. In the exemplary embodiment, the light transmissive window 216 is in the mirror aperture 214. Suitable light transmissive materials for the window are known and include, for example, aluminum oxide, quartz and magnesium fluoride.

Light transmissive window 214 can additionally be provided with a coating layer on a surface opposite the surface facing the sample region for reflecting a portion of the light beam. Subtracting the signal due to the reflected portion of the beam from that of the transmitted portion can result in more accurate absorption measurements than otherwise possible. Among the commercially available coating materials, metallic coatings are preferred.

As shown in the exemplified embodiment, light transmissive window 216 is preferably offset at an angle from perpendicular relative to the incoming light beam. While the Brewster angle is a preferred offset angle for its effectiveness, angles smaller than the Brewster angle are typically more convenient and are also effective. By offsetting the window in this manner, coherent interference caused by the reflected portion of the beam can be avoided. As a result, measurement of greater accuracy can be obtained. Such an offset can further serve the same purpose as that served by the optional coating layer described above. That is, the reflected portion of the beam can be used to obtain a more accurate measurement by subtracting out the signal due to background noise.

The cell 200 should be sealed in a substantially airtight manner, to make possible the measurement of gas samples at lower than atmospheric pressures, i.e., at vacuum conditions. As a result, in-situ measurements in vacuum processing tools such as used in the semiconductor manufacturing industry can effectively be performed. To ensure that the measurement cell remains airtight, an o-ring or some other type of vacuum seal known to those skilled in the art can be employed to seal mirror 210.

One or more purge gas flows are introduced into the cell through purge gas inlets 230, 232 to prevent the accumulation of deposits on one or more of the optical components. In the exemplified embodiment, gas inlet 230 is associated with the mirror having a light transmissive window 216, while gas inlet 232 is associated with the mirror at the opposite end of the cell. The purge gas is preferably an inert gas selected from the group consisting of nitrogen, argon, helium and combinations thereof, although oxygen, hydrogen, other reactive gases, combinations of reaction gases or combinations of inert and reactive gases can be employed. For example, in the case of $SiO_2$ deposition from SiO in the vapor phase, a hydrogen purge can reduce SiO to $SiH_4$ and $H_2O$, thereby preventing formation of $SiO_2$ deposits.

The placement, size, and upstream pressure of the purge gas inlets are designed in such a manner that the purge gas is directed over the critical surface of the optical components, with a velocity such that a critical surface of the optical component is fully swept by the purge gas flow which is essentially unmixed with the main exhaust gas flow. As used herein, the term critical surface means a portion of the optical component coming into contact with the light beam from the light source, and upon which the prevention of deposition is desired. Flow control of the purge gas is accomplished, for example, through use of a mass flow controller, an orifice with a constant upstream pressure and/or other flow control devices.

While a constant flow of the purge gas can be employed, it is also possible to employ a pulsed flow of the purge gas. Use of a pulsed flow can further minimize purge gas usage over a constant flow. Pulsed flow can be achieved using know flow control techniques, such as by use of an upstream pressure regulator followed by a ballast vessel and solenoid valve, with the solenoid valve being opened and closed for desired time periods by use of a controller.

In either case of continuous or pulsed flow, it is desirable to deliver the purge gas with sufficient velocity to sweep the entire critical surface, while minimizing the total flow of purge gas. While the purge gas flowrate will vary depending on geometry of the device, pressure and flow of sample gas, the gas flowrate is typically from about 5 to 100 sccm, but can be as high as about 10 slm where the total flow through the cell is greater than about 10 slm.

Figure 3A:
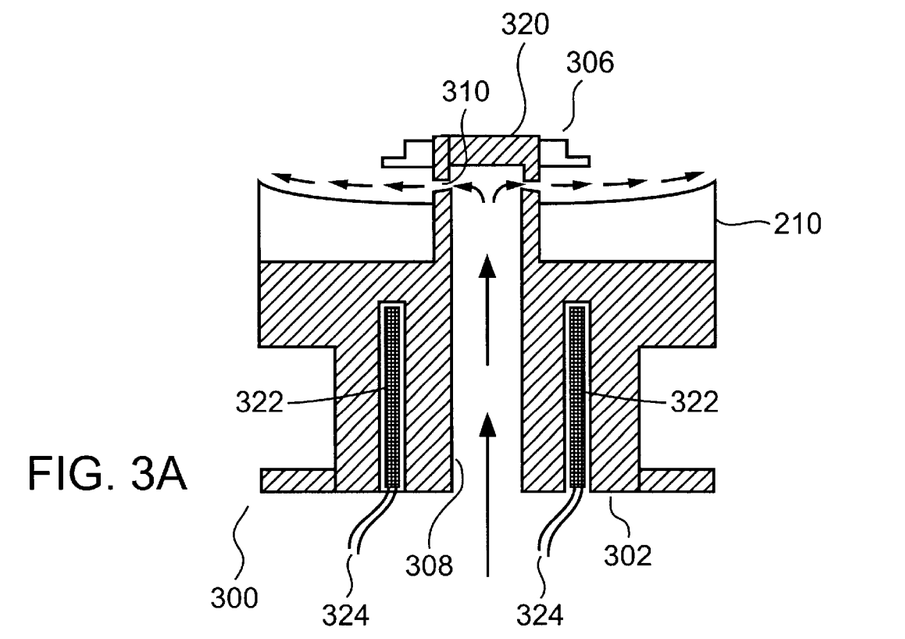
FIGS. 3A and 3B are cross-sectional views of an exemplary device, with and without a light transmissive window, for preventing deposition on an optical component, in accordance with one aspect of the invention.

FIG. 3A illustrates in greater detail a crosssectional view of an exemplary device 300 for preventing deposition on an optical component which is included in the cell of FIGS. 2A–B. Device 300 includes a mirror stage 302, a mirror 210 and a flow directing device 306. These components are illustrated in greater detail in FIGS. 4A–B, 5A–B and 6A–B, respectively.

A purge gas is introduced from a gas pipe (not shown) into device 300. The flow path through the device is shown by the arrows. As can be seen, the gas passes through a bore 308 in mirror stage 302, through a plurality of gas injection orifices 310 in stage 302 and across the front surface of mirror 210. The gas flow is in a direction substantially parallel to the front surface of the mirror. For the case where the gas pressure in the sample cell 200 is less than about 1

Torr, the gas pressure upstream of the orifices is typically from about 1 to 20 Torr. The gas pressure upstream of the orifices is preferably at least twice the pressure in the cell 200. The gas injection orifices 310 preferably have a diameter of from about 50 to 100 µm, and preferably have a diameter no larger than about 500 µm. The distance between adjacent orifices is preferably no more than about 3 mm along the circumference of the stem portion 320 of the mirror stage 302. The orifices 310 are preferably from about 0.5 to 5 mm above the mirror front surface, typically about 1 mm above the mirror front surface.

Figure 3B:
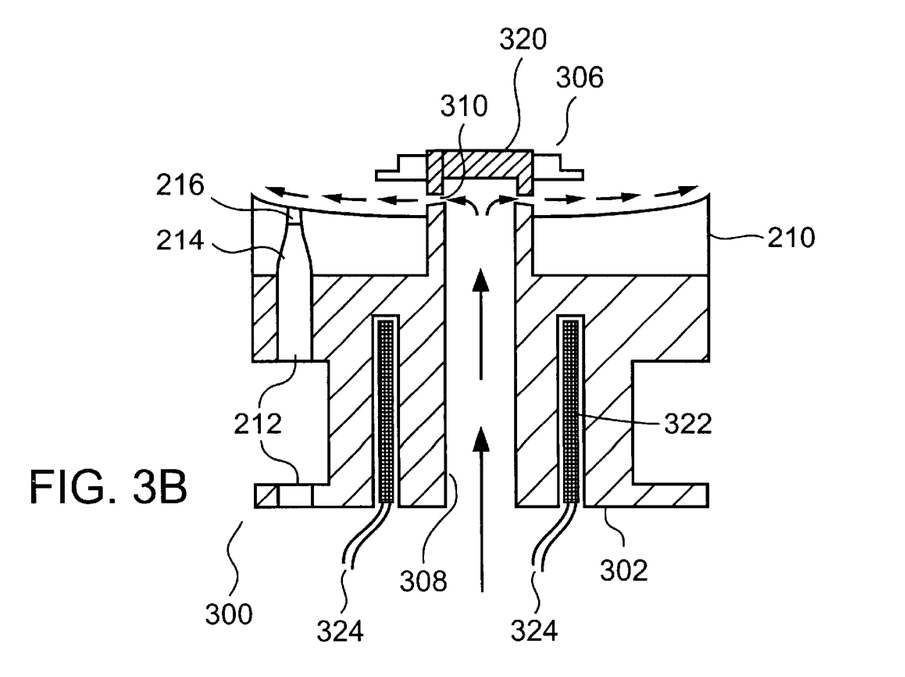

FIG. 3B is identical to 3A except that the mirror stage includes the light entry port aperture 212 in the mirror stage and the mirror aperture 216, which holds light transmissive window 216.

Figure 4A:
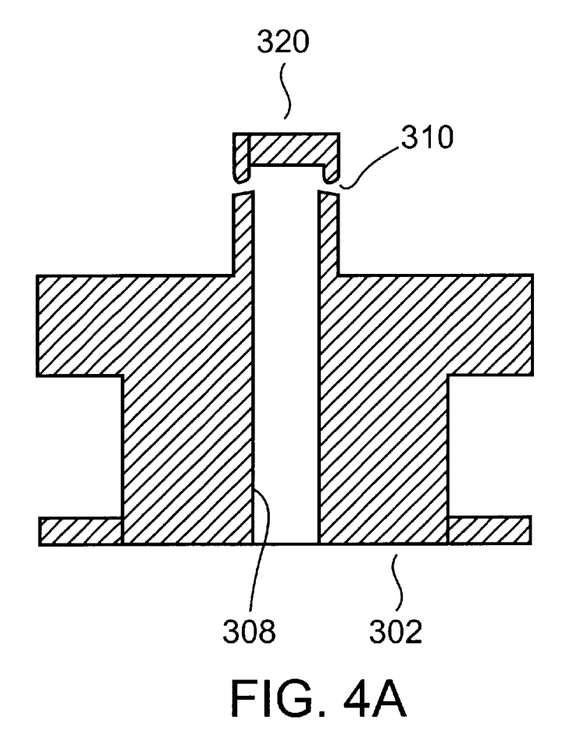
FIGS. 4A and 4B are cross-sectional and plan views, respectively, of a mirror stage of the device shown in FIG. 3.
Figure 4B:
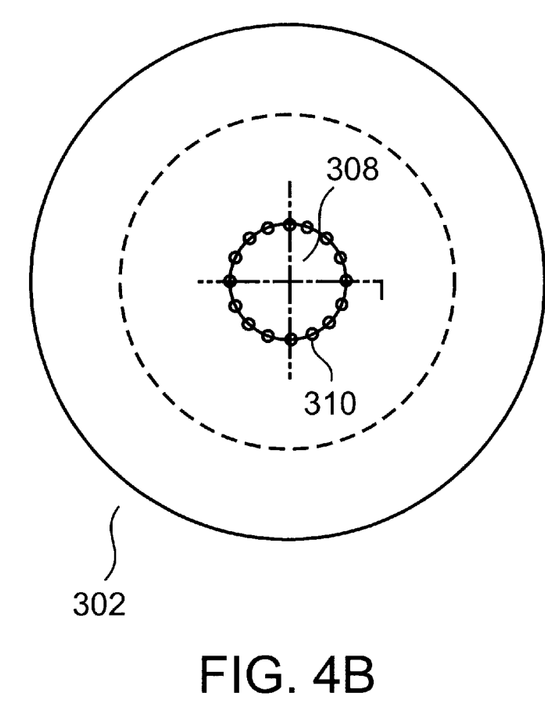

FIGS. 4A and 4B are cross-sectional and plan views, respectively, of mirror stage 302. As shown in FIG. 4B, the plurality of gas injection orifices 310 are preferably symmetrically distributed about the central axis of the mirror stage such that the ejected purge gas is swept across the critical surface of the optical component.

Figure 5A:
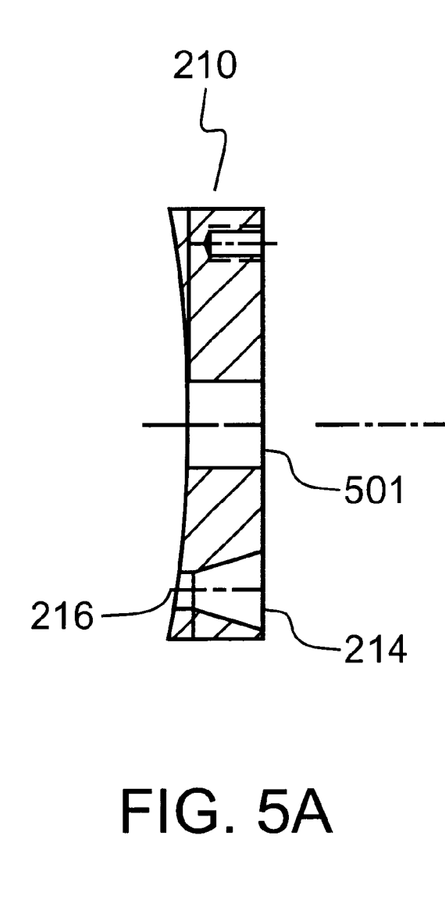
FIGS. 5A and 5B are cross-sectional and plan views, respectively, of a mirror of the device shown in FIG. 3.
Figure 5B:
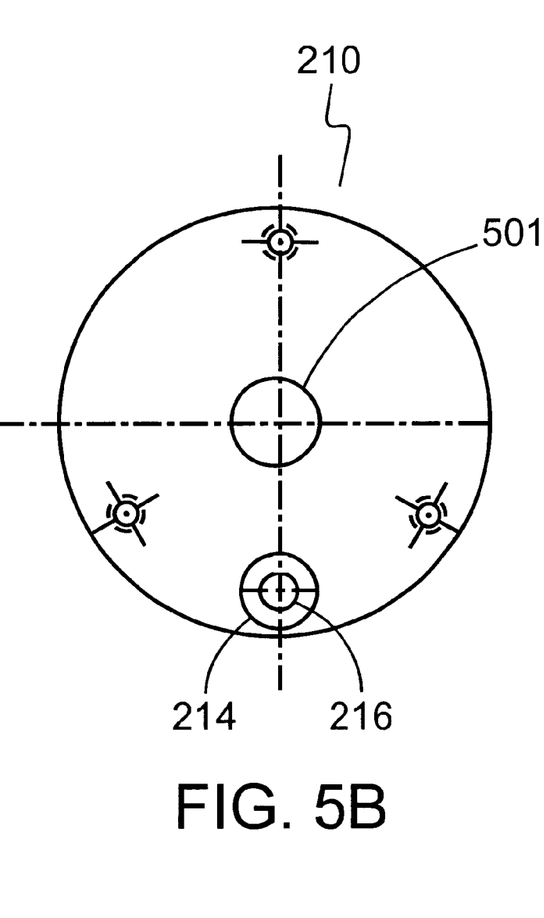

FIGS. 5A and 5B are cross-sectional and plan views, respectively, of an exemplary mirror 210 used in the deposition preventing device. Mirror 210 has an aperture 501 along the central axis which allows the mirror to be placed on the mirror stage by inserting stem portion 320 of the stage through aperture 501. An aperture 214 is also present which holds the light transmissive window 216. In the illustrated embodiment, in which a single window is employed for light entering and exiting the cell, the mirror on the opposite side of the cell is identical but with no window or aperture therefor.

Figure 6A:
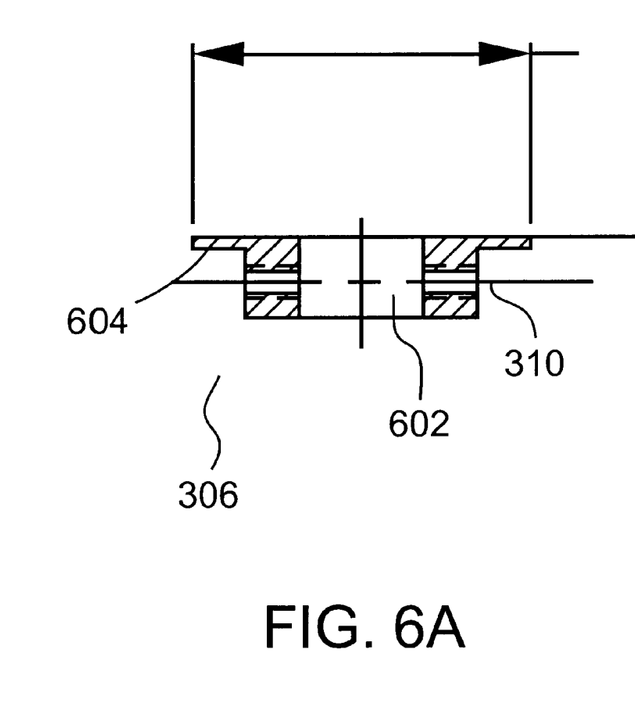
FIGS. 6A and 6B are cross-sectional and plan views, respectively, of a purge gas flow directing device shown in FIG. 2.
Figure 6B:
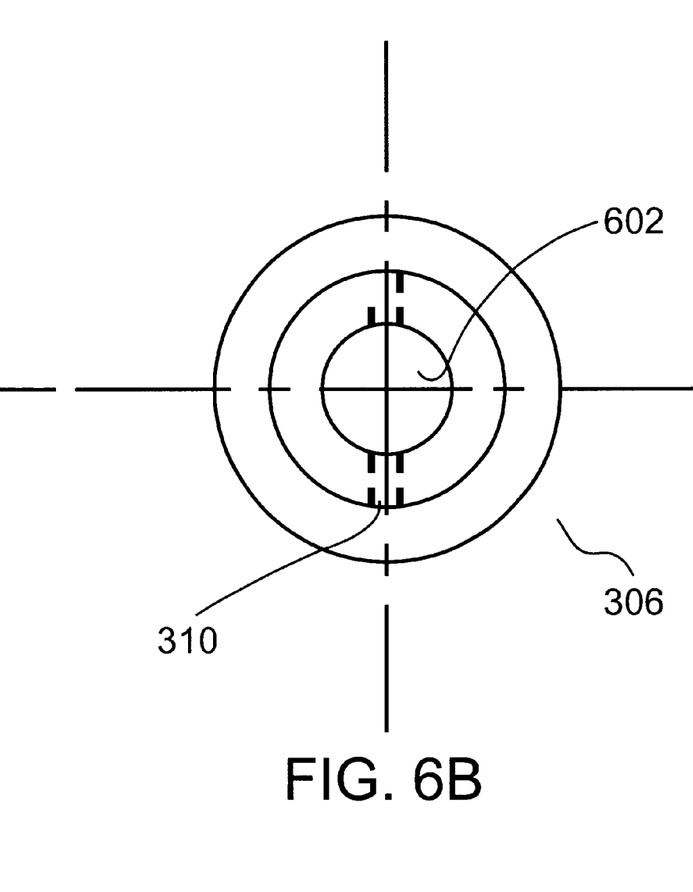

FIGS. 6A and 6B are cross-sectional and plan views, respectively, of a purge gas flow directing device 306. The geometry of the flow directing device should be selected to provide sufficient flow across the surface of the optical component to prevent unwanted deposits from accumulating on the critical surface thereof. In the exemplified embodiment, flow directing device is circular in shape, which complements the circular shaped mirrors.

Purge flow directing device includes an aperture 602 which fits over the stem portion 320 of the mirror stage 302 for attaching the flow directing device 306 to the stage. Flange portion 604 provides a surface which controllably directs the flow of the purge gas across the surface of the optical component. Preferably, the flow directing device 306 is disposed immediately above the gas injection orifices 310, preferably about 2 mm above the mirror 210 front surface, and preferably no more than about 10 mm above the mirror front surface.

The arrangement of the injection orifices 310, the mirror 210 and the gas flow directing device 306 provides a gas velocity sufficient to purge the critical mirror surface. Quite surprisingly, effective purging does not require that the velocity of the purge gas molecules in the direction parallel to the mirror surface exceed the typical molecular speed in the exhaust. For example, for an exhaust line at 25° C., the mean velocity of a molecule such as nitrogen in the exhaust is about 500 m/s (averaged over all directions).

Figure 7:
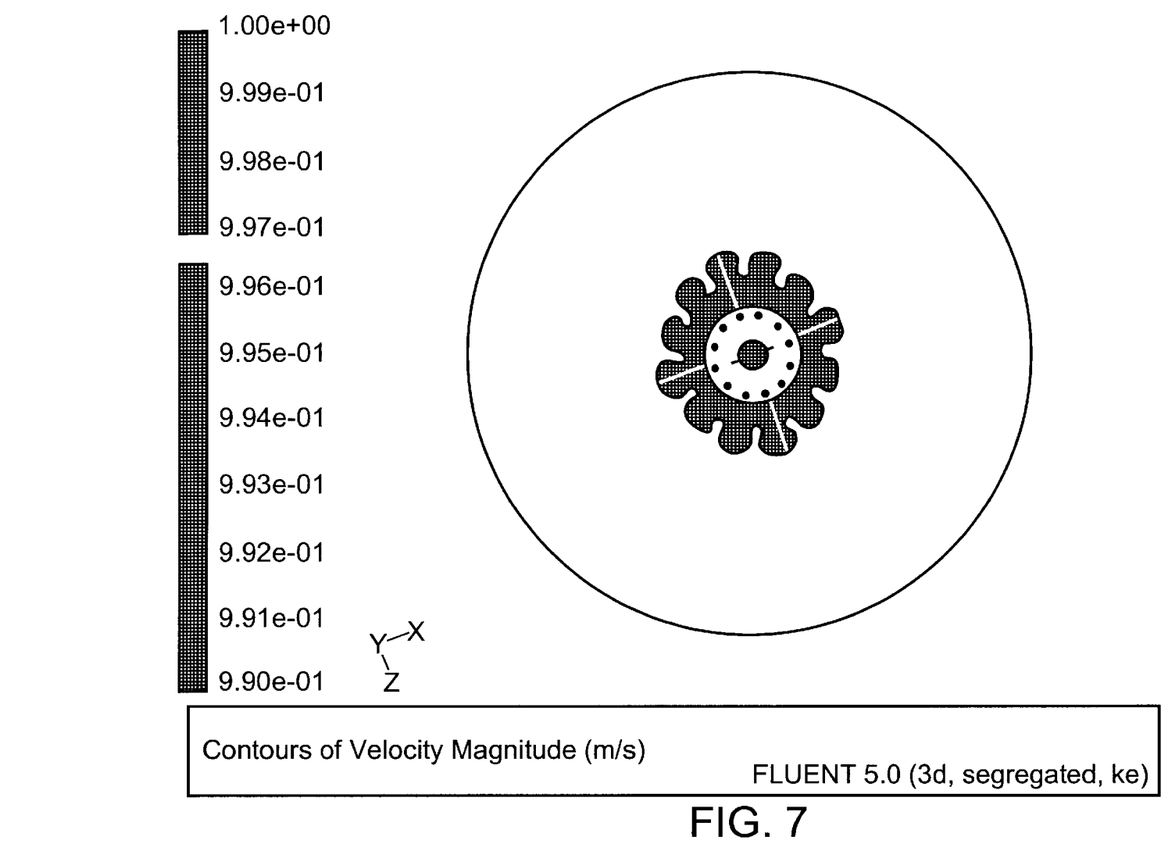
FIG. 7 is a computer simulation result for flowing a purge gas across a mirror surface.

FIG. 7 shows the results from a computer simulation for a purge gas flowing across the surface of a mirror. The simulation was obtained using typical operating conditions, including a total flowrate of 20 sccm over a single mirror. The simulation shows that the velocity contour at 1 cm from the purge gas source is about 1 m/s.

It is believed that this result can be explained by making the simplifying assumption that the purged region corresponds to a cylinder 3 mm in height at the mirror surface. In this case, for a 20 sccm flow over the mirror surface, the total molecular flux at a 1 cm radius is about $1.7 \times 10^{-3}$ atm m/s. The simulation result indicates that the local number density at the mirror surface is equivalent to about 1 torr. Under this condition, the mean free path of a molecule is about 1 µm. Thus, a molecule in the exhaust which penetrates the purge gas flow will undergo about 3000 collisions. It is, therefore, believed that although the velocity of the purge gas molecules in the purge direction is significantly less than the velocity of an impinging molecule, it is sufficient to maintain the mirror surface clean due to the large number of purge gas collisions an impinging molecule must undergo.

The mirror purge arrangement described herein has been found effective in protecting optics from accumulating deposits and from chemical attack due to gas phase reactive species in the exhaust line. If particles are also present, additional measures may be desirable. A sufficiently large particle moving with sufficient velocity will penetrate the purge gas flow while a molecule with the same velocity may not. Where deposition due to particles is an issue, it is preferred that optics be placed at right angles to the exhaust gas flow and/or to set the optics back slightly therefrom. If the optics are perpendicular to the gas flow, a set-back of about 1 cm or more is generally sufficient, although a set-back of up to about 12 cm can typically be used.

In the exemplary configuration shown in FIG. 2, the downstream mirror is perpendicular to the gas flow but the upstream mirror is not. To minimize deposition on the upstream mirror surface in such a case, the downstream mirror can be set further back from the cell outlet, for example, about 12 cm or more, from the cell outlet. If this setback geometry is optimized, particles will not penetrate the purge gas flow.

Advantageously, the purge gas inlet is used in conjunction with a circular mirror. With a circular mirror as illustrated which is typically used in a Herriott cell, the critical surfaces are close to the circumference and the center is optically unimportant. Thus, the purge gas inlet can be disposed at a center portion of the mirror, thereby feeding the purge gas from the center of the mirror outward towards the periphery.

In a further refinement, if the entire periphery is not used, the purge gas can be directed to cover the most critical portions of the periphery. For example, in a Herriott-type cell, light strikes the mirror in a circular multi-spot pattern. The purge gas introduction system can be constructed such that there are one or more orifices corresponding to each spot, and directing the purge gas flow over the spot portion. Other designs can also be instituted. For example, square, rectangular or other shaped mirrors can be employed in the invention.

In addition, purge gas schemes other than those described above can be employed. For example, the use of a purge gas flow from the outer periphery of the optical component towards the central axis thereof is envisioned, especially for cells in which the center of the cell is used, for example, in intra-cavity and cavity ring-down spectroscopic cells. In such case, it is desirable to maintain the mirror center in a deposit free state.

As a result of the invention, the purge gas injector geometry is such that the gas can be directed onto the critical surfaces. As a result, the flowrate of the purge gas can be minimized, which is particularly desirable in the case of vacuum processing apparatus as the pumping requirements would not be adversely affected. Localization of the flow of the gas in the vicinity of the critical surface minimizes the flow of the purge gas. As a result, the need for retrofitting vacuum systems with larger capacity pumps can be eliminated.

In accordance with a further aspect of the invention, the optical component can be heated. This can advantageously aid in the prevention of deposition on the optical component in certain circumstances. Typically, the optical surface can be heated to a temperature of from about 50 to 150° C., preferably from about 70 to 100° C., although optimal temperatures are process dependent. The heating can be direct or indirect. Typical optical surface heating structures and methods are described in U.S. Pat. No. 5,949,537, to McAndrew et al, and U.S. Pat. No. 6,084,668, to Inman et al, the entire contents of which documents are incorporated herein by reference.

In the case of indirect heating, the mirror stage can be heated, which in turn heats the optical surface. Suitable heaters include, but are not limited to resistance-type heaters, self-regulating-type heaters such as heat trace, heating lamps, inductive heaters and liquid or gaseous heating fluids which can optionally be recirculated. An example of such a structure is illustrated in FIGS. 3A and 3B, which show a resistance-type cartridge heater 322 embedded in the mirror stage 302. Electrical leads 324 are connected at one end to the heating element of the cartridge heater 322 and at the other end to a voltage source.

Additionally or alternatively, the purge gas can be heated, Preferably, such heated gas is localized on the window or light reflective surface of the mirror to effectively prevent deposits on the optical component critical surfaces. The purge gas can be heated prior to being introduced into the cell using, for example, a resistance heater or other heat exchange techniques known to those skilled in the art.

Although the exemplified in-line cell is of a Herriott design, the inventive concepts can readily be applied to other types of in-line cells. For example, the inventive concepts can be applied to polygonal multipass cells or to any form of cell which is amenable to the above conditions with respect to the optical component and purge structures.

The in-line cell should be constructed of materials which are compatible with the atmospheres being contained therein. Such materials are within the knowledge of persons skilled in the art. For example, various forms of stainless steel can be used for cell surfaces which contact the sample being measured.

Figure 8:
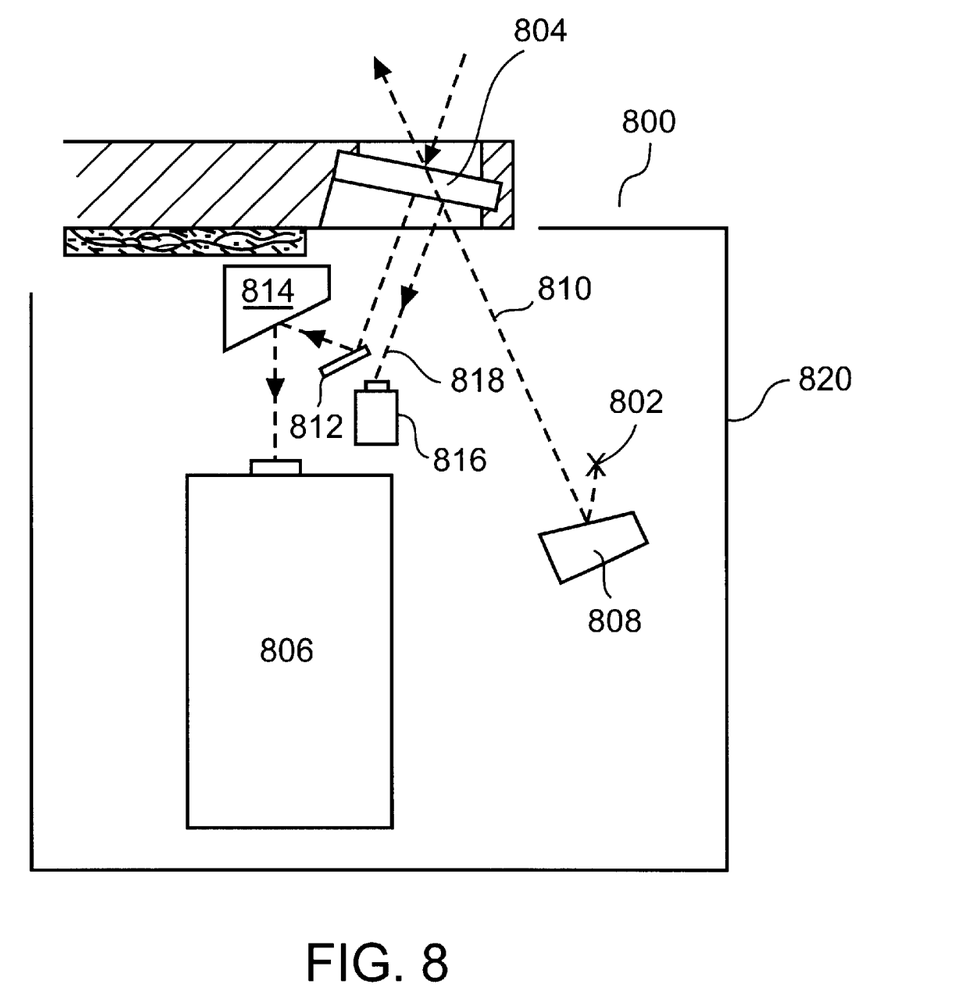
FIG. 8 is a top view of a light source/detector scheme in an apparatus for performing an absorption spectroscopy measurement in accordance with a further aspect of the present invention.

While the inventive cell can be used for any absorption spectroscopy technique, it is preferably used in laser spectroscopy and, particularly, tunable diode laser absorption spectroscopy (TDLAS). With reference to FIG. 8, such an apparatus 800 includes, in addition to the in-line cell as described above with reference to FIGS. 2A and 2B, a light source 802, preferably a diode laser, for generating a light beam which is directed through the light transmissive window 804 into the sample region of the cell. To measure the light beam which exits the cell through the light transmissive window, the apparatus further includes a main detector 806, which can be, for example, a photodiode.

Any molecular impurity of interest can be detected, subject only to the availability of a suitable light source. For example, water vapor, nitric oxide, carbon monoxide, hydrogen fluoride, silicon tetrafluoride and other fluorides, and methane and other hydrocarbons can be detected by measuring the attenuation of light from a diode laser source which emits light of a wavelength characteristic of the impurity.

Laser light sources which emit light in spectral regions where the molecules of interest absorb most strongly lead to improvements in measurement sensitivity. In particular, light sources which emit at wavelengths longer than about 2 $\mu$m are preferred, since many of the molecular impurities of interest have strong absorption bands in this region.

Any suitable wavelength-tunable light source can be used. Of the currently available light sources, diode laser light sources are preferred because of their narrow linewidth (less than about $10^{-3}$ cm$^{-1}$) and relatively high intensity (about 0.1 to several milliwatts) at the emission wavelength.

Examples of diode lasers include Pb-salt and GaAs-type diode lasers. The Pb-salt-type laser requires cryogenic temperatures for operation and emits infrared light (wavelength greater than 3 $\mu$m), while the GaAs-type diode laser can operate at close to room temperature and emits in the near infrared region (0.8–2 $\mu$m).

Recently, diode lasers which include Sb in addition to GaAs (or other pairs of III–V compounds such as AsP) have been described (see, "Mid-infrared wavelengths enhance trace gas sensing," R. Martinelli, Laser Focus World, March 1996, p. 77). These diodes emit light of a wavelength greater than 2 $\mu$m while operating at −87.8° C. While such a low temperature is not convenient, it compares favorably with the cryogenic temperatures (less than −170° C.) required by Pb-salt lasers.

Operation of similar lasers at 4 $\mu$m and 12° C. has also been reported (see, Lasers and Optronics, March 1996). Diode lasers of the above described type will most preferably operate at temperatures of at least −40° C. Use of a thermoelectric cooler for temperature control at such temperatures makes these light sources less complicated than the lower temperature diode systems.

To make use of these lasers more advantageous, improvement in the optical properties over current levels is important. For example, single mode diodes (i.e., diodes whose emission at fixed temperature and drive current is at a single wavelength with emission at other wavelengths at least 40 dB less intense) should be available.

Suitable light sources for use in the invention are not limited to the above described diode lasers. For example, other types of lasers which are similarly sized and tunable by simple electrical means, such as fiber lasers and quantum cascade lasers, are envisioned. The use of such lasers as they become commercially available is envisioned.

The apparatus can further include at least one mirror 808 or a lens for reflecting the light beam 810 from the light source 802 through the light transmissive window into the cell, and at least one additional mirror 812, 814 for reflecting the light beam exiting the cell to the main detector. Lenses may optionally be used in place of mirrors 808 and 814.

The mirror 808 is preferably curved in order to collimate the light beam as the light from the diode laser source is divergent. Likewise, mirror 814 is preferably curved in order to focus the parallel light beam on the main detector.

A second detector 816, which can also be a photodiode, for measuring a portion of the light beam 818 which is reflected from the light transmissive window 804 as well as means for subtracting this reference signal from a measurement obtained by the main detector can optionally be provided in the apparatus. An operational amplifier in a configuration such as described in the literature (See, e.g., Moore, J. H. et al "Building Scientific Apparatus", Addison Wesley, London, 1983) can act as the means for subtracting the reference signal.

The reflected light does not show any absorption by the molecules of interest in the sample region, and therefore provides a reference signal. By subtracting the reference signal from that of the light which passes through the cell (which is measured by the main detector), variations in the light source can be compensated for. This also allows for enhanced sensitivity to signal changes due to molecules in the system chamber 820.

While "dual beam" techniques using subtraction of a reference beam are well-known they usually require a dedicated beam-splitter, i.e., an optical element whose only function is to divide the light beam. According to the present invention, the entrance window to the chamber can provide this function without the need for any additional components. The ratio of transmitted to reflected light at this window can be controlled by use of an appropriate coating for the window.

The inventive apparatus has particular applicability in detecting and/or measuring concentration of a molecular species in a gas exhausted from a vacuum chamber. In such a case, the cell can be disposed in a vacuum exhaust line between a vacuum chamber and a vacuum pump system.

The apparatus is compatible with a wide range of materials. For example, the vacuum chamber can contain certain reactive or non-reactive (inert) gas species which can be in a plasma- or non-plasma state. Examples of reactive gases which are compatible with the inventive apparatus include $H_2$, $O_2$ and, provided the moisture level is less than 1000 ppm, $SiH_4$, $HCl$, and $Cl_2$. Any inert gas such as, e.g., $N_2$, Ar, Ne or He, can be used in the inventive apparatus. In the case the inventive apparatus is used in a plasma environment, the apparatus is preferably mounted about 6 inches or more away from the plasma zone in order to minimize the formation of deposits on the windows and other cell surfaces.

Because the detection apparatus described above can be used in plasma or non-plasma atmospheres as well as with inert or reactive gases, the apparatus is particularly well suited for use in monitoring gas phase molecular species, such as water vapor, in a semiconductor processing apparatus. Use of the detection apparatus in conjunction with a semiconductor processing apparatus allows for real time in-situ monitoring of gas phase molecular impurities.

The apparatus can be readily adapted to virtually any semiconductor processing apparatus which employs a vacuum system. Examples of such apparatuses include etching, diffusion, chemical vapor deposition (CVD), ion implantation, sputtering and rapid thermal processing apparatuses.

Figure 9:
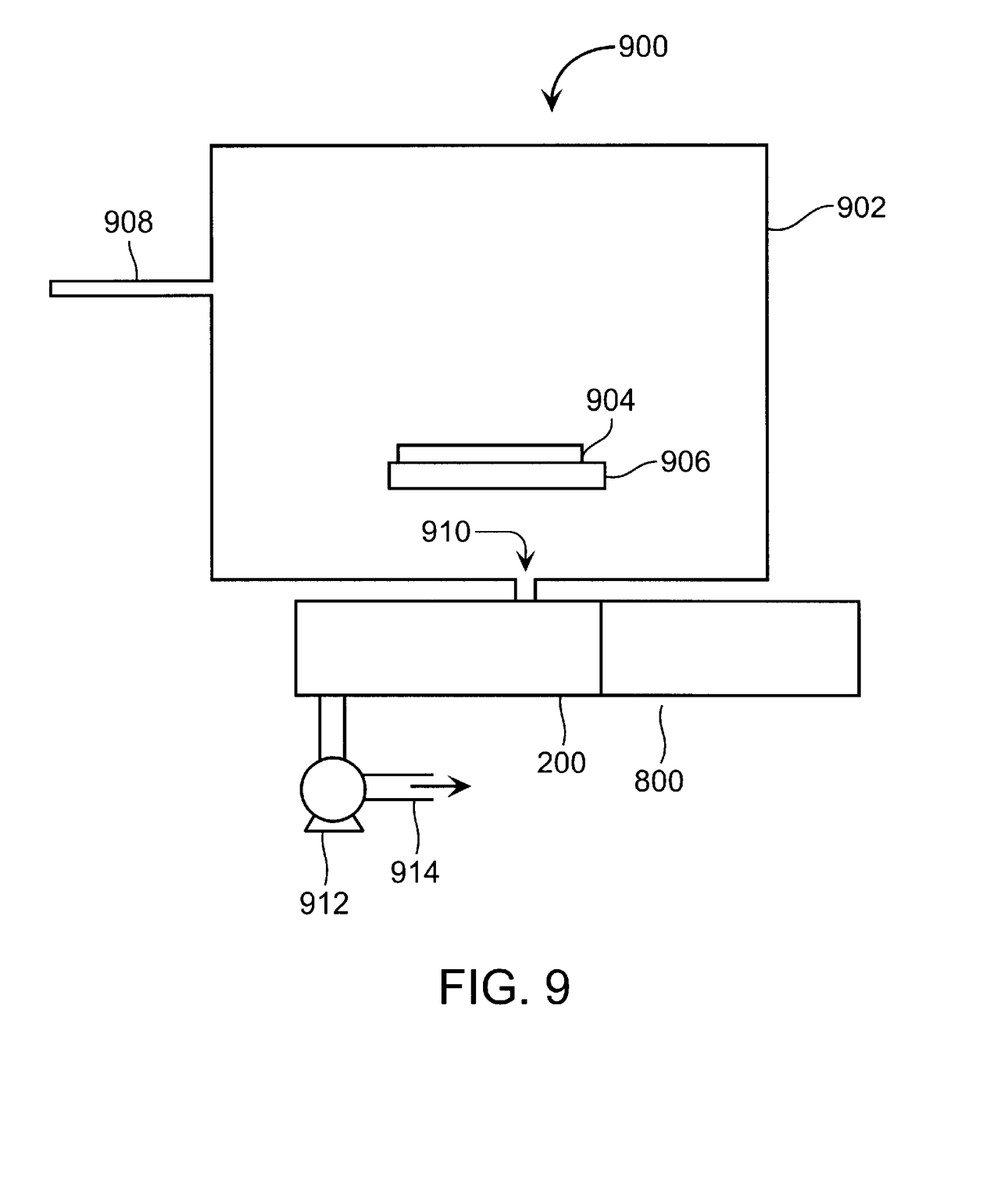
FIG. 9 is a side sectional view of a semiconductor processing apparatus in accordance with a further aspect of the invention.

FIG. 9 illustrates a semiconductor processing apparatus 900 which comprises an in-line cell 200 and apparatus 800 for performing absorption spectroscopy measurements as described in detail above. The apparatus further includes a vacuum chamber 902 inside which a semiconductor substrate 904 is disposed on a substrate holder 906. One or more gas inlets 908 are provided for delivering a gas or plural gases to the vacuum chamber.

The vacuum chamber is evacuated through an exhaust opening 910 in the vacuum chamber. A portion of the total exhaust from the processing tool or the entire exhaust volume can be introduced into cell 911. A vacuum pump 912 for evacuating the vacuum chamber is connected thereto, either directly or through a vacuum line. A pump exhaust line 914 can be connected to the pump 912, which can be connected to another pump or to a gas scrubber (not shown). Examples of vacuum pumps which may be employed are mechanical rotary and booster pumps, diffusion pumps, cryogenic pumps, sorption pumps and turbomolecular pumps.

Furthermore, while the vacuum pump and measurement apparatus have been illustrated as being disposed below the vacuum chamber, those skilled in the art readily understand that other orientations are also possible.

While the invention has been described in detail with reference to specific embodiments thereof, it will be apparent to one skilled in the art that various changes and modifications can be made, and equivalents employed, without departing from the scope of the appended claims.

What is claimed is:

1. A method of preventing deposition on an optical component in an absorption spectroscopy measurement cell, comprising:

performing an absorption spectroscopy measurement of a sample gas introduced into the cell; and introducing a flow of purge gas from a purge gas inlet pipe across a critical surface of the optical element at a velocity effective to prevent deposition on the critical surface, wherein the gas inlet is disposed adjacent said critical surface, and wherein the purge gas is introduced from the purge gas inlet pipe at a flowrate of from about 5 to 100 sccm.

2. The method according to claim 1, wherein the flow of purge gas being introduced across the critical surface is pulsed.

3. The method according to claim 1, wherein the optical element is a mirror.

4. The method according to claim 3, wherein the cell is a Herriott-type cell.

5. The method according to claim 1, wherein the purge gas flows across the critical surface in a direction from a central axis of the optical element towards the outer periphery thereof.

6. The method according to claim 5, wherein the purge gas inlet pipe comprises a plurality of purge gas injection orifices through which the purge gas flows.

7. The method according to claim 6, wherein the plurality of purge gas injection orifices are disposed above the critical surface and inject the purge gas in a direction substantially parallel to the critical surface.

8. The method according to claim 7, wherein the gas inlet is circular in cross-section, and the plurality of purge gas injection orifices are substantially evenly distributed along the circumference of the gas injector.

9. The method according to claim 1, wherein the purge gas inlet pipe comprises a plurality of purge gas injection orifices through which the purge gas flows.

10. The method according to claim 1, wherein the purge gas is an inert gas selected from the group consisting of nitrogen, argon, neon, helium and combinations thereof.

11. The method according to claim 1, wherein the purge gas is a reactive gas or a combination of a reactive gas and an inert gas.

12. The method according to claim 11, wherein the reactive gas is oxygen or hydrogen.

13. The method according to claim 1, further comprising heating the critical surface of the optical element to a temperature of from about 50 to 150° C.

14. The method according to claim 1, wherein the sample gas is introduced into the cell through a sample gas inlet and is removed from the cell through a sample gas outlet, thereby establishing a flow path for the sample gas through the cell, wherein the critical surface of the optical element is set back from the flow path.

15. The method according to claim 1, wherein the sample gas is introduced into the cell through a sample gas inlet from a semiconductor processing chamber.

16. A device for preventing deposition on an optical component useful in an absorption spectroscopy measurement cell, comprising a purge gas inlet pipe for introducing a flow of purge gas across a critical surface of the optical element at a velocity effective to prevent deposition on the critical surface, wherein the gas inlet is disposed adjacent said critical surface, and wherein the purge gas inlet pipe comprises a plurality of purge gas injection orifices through which the purge gas flows.

17. The device according to claim 16, further comprising means for pulsing the flow of purge gas being introduced across the critical surface.

18. The device according to claim 16, wherein the gas inlet pipe is disposed along a central axis of the optical element, such that the purge gas flows across the critical surface in a direction from the central axis towards an outer periphery of the optical element.

19. The device according to claim 18, wherein the plurality of purge gas injection orifices are disposed above the critical surface and inject the purge gas in a direction substantially parallel to the critical surface.

20. The device according to claim 19, wherein the gas inlet is circular in cross-section, and the plurality of purge gas injection orifices are substantially evenly distributed along the circumference of the gas injector.

21. The device according to claim 20, further comprising a flow directing device for directing the flow of the purge gas from the gas inlet across the critical surface.

22. The device according to claim 21, wherein the flow directing device is disposed above the critical surface and the gas injection orifices.

23. The device according to claim 22, wherein the optical element is a mirror.

24. The device according to claim 16, further comprising a heater for heating the critical surface of the optical element.

25. The device according to claim 24, further comprising a stage on which the optical element is disposed wherein the heater is connected to the stage.

26. The device according to claim 24, wherein the optical element is a mirror.

27. A measurement cell useful in absorption spectroscopy measurement, comprising a sample gas inlet, a sample gas outlet and a sample region, a light entry port and a light exit port being the same or separate ports, each said port being in optical communication with the sample region and containing a light transmissive window; and the device for preventing deposition on an optical component in accordance with claim 16.

28. The measurement cell according to claim 27, wherein the inlet and outlet establish a flow path for the sample gas to pass through the cell, wherein the critical surface of the optical element is set back from the flow path.

29. An apparatus for performing an absorption spectroscopy measurement, comprising the measurement cell according to claim 27, a light source for generating a light beam which passes through the light entry port into the cell, and a detector for measuring the light beam exiting the cell through the light exit port.

30. The apparatus according to claim 29, wherein the absorption spectroscopy measurement apparatus is a tunable diode laser absorption spectroscopy measurement apparatus, an intra-cavity spectroscopy measurement apparatus or a cavity ring-down spectroscopy measurement apparatus.

31. A semiconductor processing apparatus, comprising:
a semiconductor processing apparatus comprising a substrate processing chamber and an exhaust line connected thereto, and the apparatus for performing an absorption spectroscopy measurement according to claim 27.

* * * * *